United States Patent [19]

Lahaije et al.

[11] Patent Number: 5,359,668
[45] Date of Patent: Oct. 25, 1994

[54] METHOD AND APPARATUS FOR DETERMINING THE IMAGE CLARITY OF A SURFACE

[75] Inventors: Christiaan T. W. Lahaije, Heerhugowaard; Wilhelmus J. van der Meer, Amsterdam, both of Netherlands

[73] Assignee: Hoogovens Groep B.V., Ijmuiden, Netherlands

[21] Appl. No.: 946,440

[22] PCT Filed: May 17, 1991

[86] PCT No.: PCT/EP91/00932

§ 371 Date: Nov. 18, 1992

§ 102(e) Date: Nov. 18, 1992

[87] PCT Pub. No.: WO91/18278

PCT Pub. Date: Nov. 28, 1991

[30] Foreign Application Priority Data

May 18, 1990 [NL] Netherlands .................... 9001164

[51] Int. Cl.$^5$ .................................... G01N 21/55
[52] U.S. Cl. .................................... 382/8; 356/237; 356/446; 250/572
[58] Field of Search ............... 382/8, 58, 65, 69, 50, 382/51, 52, 53, 61; 356/237, 371, 310, 445, 446; 358/101, 106, 107; 250/572

[56] References Cited

U.S. PATENT DOCUMENTS

| | | | |
|---|---|---|---|
| H999 | 12/1991 | Merkel et al. | 382/8 |
| 4,682,041 | 7/1987 | Egami et al. | 250/571 |
| 4,863,268 | 9/1989 | Clarke et al. | 358/106 |
| 4,975,972 | 12/1990 | Bose et al. | 382/51 |
| 5,130,555 | 7/1992 | Suzuki et al. | 356/237 |
| 5,142,648 | 8/1992 | Fitts et al. | 356/446 |
| 5,155,558 | 10/1992 | Tannenbaum et al. | 382/8 |
| 5,208,766 | 5/1993 | Chang et al. | 356/445 |

FOREIGN PATENT DOCUMENTS

0374977 6/1990 European Pat. Off. .
3919893 12/1989 Fed. Rep. of Germany .
8503776 8/1985 PCT Int'l Appl. .

OTHER PUBLICATIONS

Feinwerktechnik & Messtechnik, vol. 93, No. 1, Jan.-Feb. 1985, (Munich DE), H. Marguerre: "Automatisierte Qualitatsprufung glanzender Oberflachen an Gebrauchsgegenstadnen durch strukturierte Beleuchtung", pp. 35–37. See pages 35–37.

Applied Optics, vol. 21, No. 16, Aug. 1982, Optical Society of America, (New York, US), H. W. Lippincott et al.: "Optical-digital detection of dents and scratches on specular metal surfaces", pp. 2875–2881, see pages 2875–2877.

IBM Technical Disclosure Bulletin, vol. 14, No. 1, Jun. 1971, (New York, US), C. H. Hammond et al.: "Detecting surface deformities", pp. 49–50, see pages 49–50.

Patent Abstracts of Japan, vol. 5, No. 201 (P-94[873], 19 Dec. 1981, & JP-A-56 122 906 (Hitachi Maxell K.K.) 26 Sep. 1981, see abstract.

*Primary Examiner*—Stephen Chin
*Assistant Examiner*—Timothy J. May
*Attorney, Agent, or Firm*—Stevens, Davis, Miller & Mosher

[57] ABSTRACT

Method for determining the image clarity of a surface of a sheet strip or similar, including projection of an image on the surface, detection of a virtual image of the image projected onto the surface and the processing of the detected virtual image into a signal which is presented as a measure for the image clarity of the surface, wherein the image reflected onto the surface is composed of a two-dimensional array of distinct light spots, whereby the processing of the detected virtual image includes the steps of (i) digitizing the detected virtual image with reference to at least one greyness discriminator value, and (ii) determining, for the greyness discriminator value, the number of distinct light spots in the digitized detected virtual image, and from steps (i) and (ii) obtaining a signal measuring image clarity of the whole area of the surface illuminated by the image projected onto the surface.

8 Claims, 5 Drawing Sheets

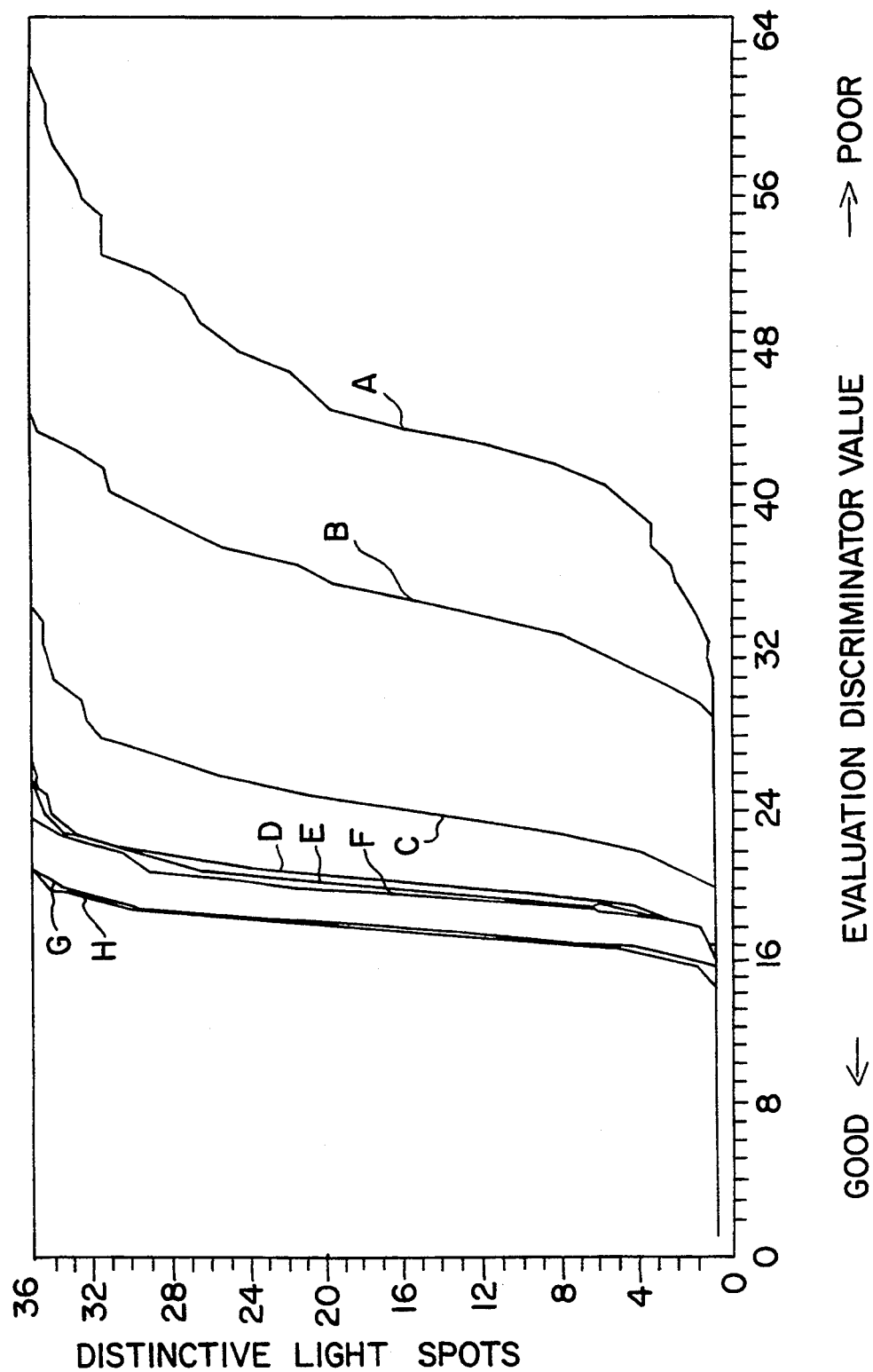

METHOD AND APPARATUS FOR DETERMINING THE IMAGE CLARITY OF A SURFACE

BACKGROUND OF THE INVENTION

The invention relates to a method for determining the image clarity of a surface of a sheet, strip or similar, comprising reflection of an image on the surface, detection of a virtual image of the image projected onto the surface and the processing of the detected virtual image of the image projected onto the surface into a signal that is presented as a measure for the image clarity of the surface.

At the same time the invention relates to an apparatus for carrying out such a method.

In the refrigerator, washing machine and automotive industries it is desirable to know the degree of image clarity of a sheet given that the sheet used for the external parts of refrigerators and washing machines, or of cars must be particularly flat and smooth because of the optical quality after painting. Indeed it has been found that there is a quality aspect of the sheet used to be found in this image clarity of the surface of the steel sheet used. In this connection image clarity is the term known in the above-mentioned industries for describing the degree of distortion of a virtual image of an image projected onto the surface. In the case of a surface with a relatively poor image clarity, the outward appearance of the steel sheet used looks somewhat irregular after painting. This phenomenon is known as orange peel. For reasons of cost it is desirable at the earliest possible processing stage and preferably before painting to select the steel sheet for suitability for any exterior parts of white goods or cars which are visible. Consequently it is desirable to have a related measuring method which is reliable and reproducible and which excludes any subjective elements.

Use is known, for example of the reflectometer by ATI Systems Inc., model 1792, whereby a controlled light beam is projected onto the surface being examined and the light reflected is received by a receiver unit and converted by a processor unit into a signal that is a measure for the brilliance of the surface.

It has been found that this known method and apparatus is not very discerning and has little value in predicting the orange peel aspect in a sheet to be used for exterior parts. In addition, the value of the information obtained with the known method and apparatus depends greatly on an operator's interpretation of the data obtained.

The object of the invention is to create a reliable method for determining the image clarity of a surface which method has a good prediction value and does not depend on subjective aspects. To this end the method in accordance with the invention is characterised in that the image reflected onto the surface is composed of a number of distinctive light spots and in that the number of distinctive light spots is determined from the virtual image detected, which number determines, at least in part, the magnitude of the signal that is produced as a measure for the image clarity of the surface.

SUMMARY OF THE INVENTION

In a specific aspect of the method in accordance with the invention it is characterised in that the detected virtual image of the image projected onto the surface undergoes an image treatment, whereby the virtual image is split into a discrete number of image points and per image point a discrete grey value is determined dependent on the light intensity of the virtual image detected at the position of that image point, and in that the number of distinctive light spots of the virtual image is determined by further treatment of the grey values pertaining to the image points.

The simplicity of the treatment of the reflected image is made use of in that subsequently the virtual image of the image projected onto the surface is transformed into a binary image by determining a binary value for each image point by comparing the grey value determined at each image point with an adjustable discriminator value and where the grey value of that image point is equal or greater in relation to the discriminator value, by adjusting the binary value pertaining to that image point to a first of the binary values, and where the grey value of that image point is smaller in relation to the discriminator value, by adjusting the binary value pertaining to that image point to a second of the binary values.

In accordance with a specific aspect of the invention the discriminator value is varied from a lowest to a highest value, and for each discriminator value the pertinent number of distinctive spots is determined in the binary image of the virtual image of the image projected onto the surface, and the signal that is presented is a measure of the image clarity of the surface, dependent on the relationship found between the discriminator values and the number of spots in the binary image.

A very simple embodiment of the method in accordance with the invention is characterised in that the discriminator value is adjusted and varied until the number of distinctive spots in the binary image of the virtual image of the image projected onto the surface is equal to the number of distinctive light spots which compose the image projected onto the surface, and in that the discriminator value pertaining to this is the signal that is presented as a measure for the image clarity of the surface.

The invention also relates to an apparatus for determining the image clarity of a surface of a sheet, strip or similar, comprising means for reflecting an image on the sheet, a receiver unit for detecting a virtual image of the image projected onto the surface and a processor unit provided with an output unit, which receiver unit is control linked with the processor unit, and which apparatus is characterised in that the processor unit is a computer which is provided with a program for carrying out the method in accordance with the invention.

BRIEF DESCRIPTION OF THE DRAWING

The invention will be illustrated in the following by reference to the drawing of a non-limitative example embodiment.

FIG. 3 shows a further example of results of use of the invention on different objects.

DESCRIPTION OF THE PREFERRED EMBODIMENT

Figure 1:
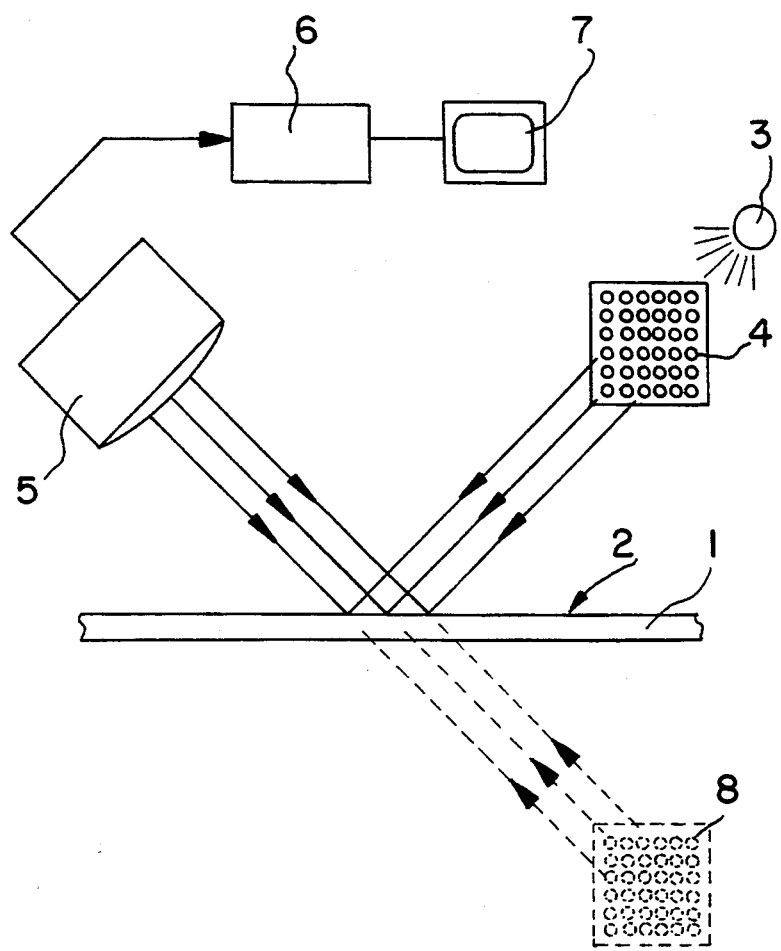
FIG. 1 shows an arrangement with the apparatus in accordance with the invention.
Figure 2B:
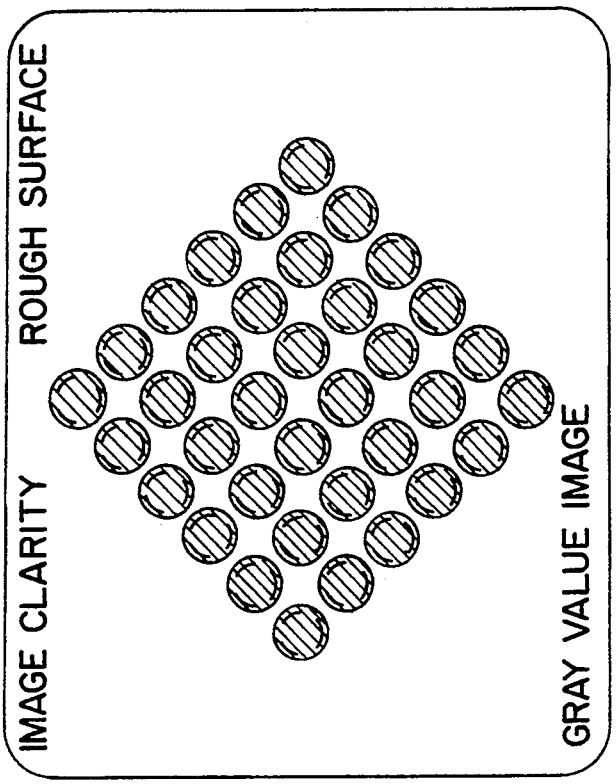
FIGS. 2a-f show examples of the result of an image treatment.
Figure 2A:
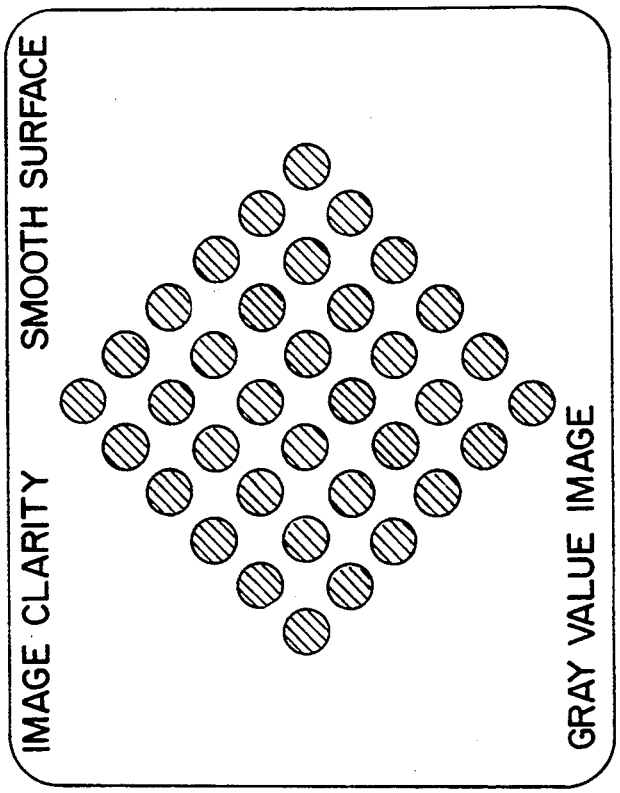
Figure 2D:
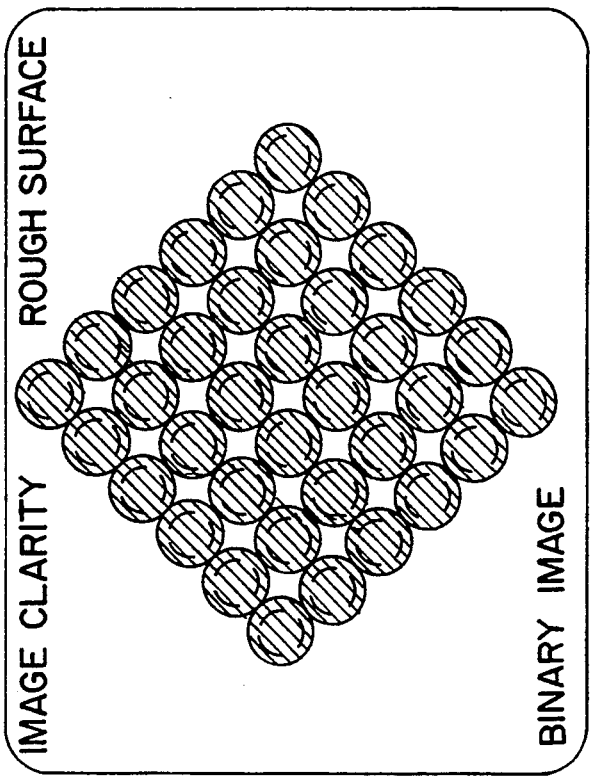
Figure 2C:
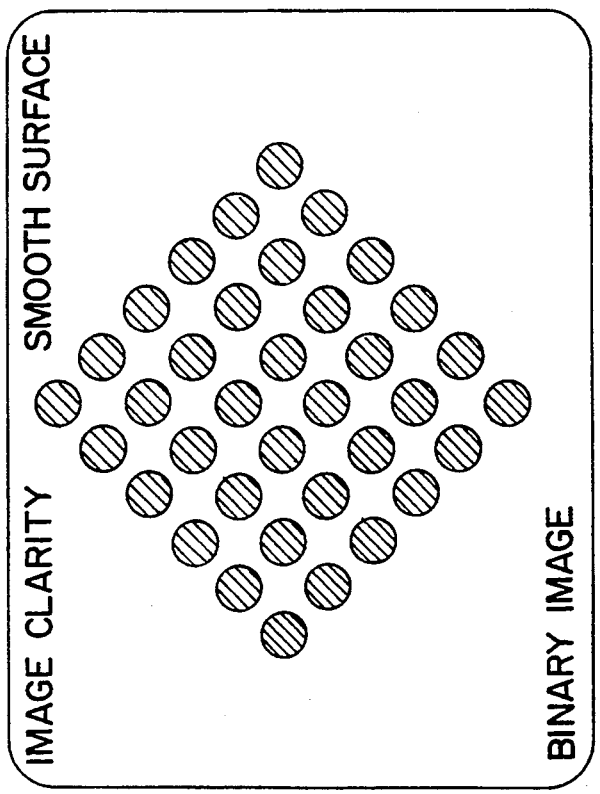
Figure 2F:
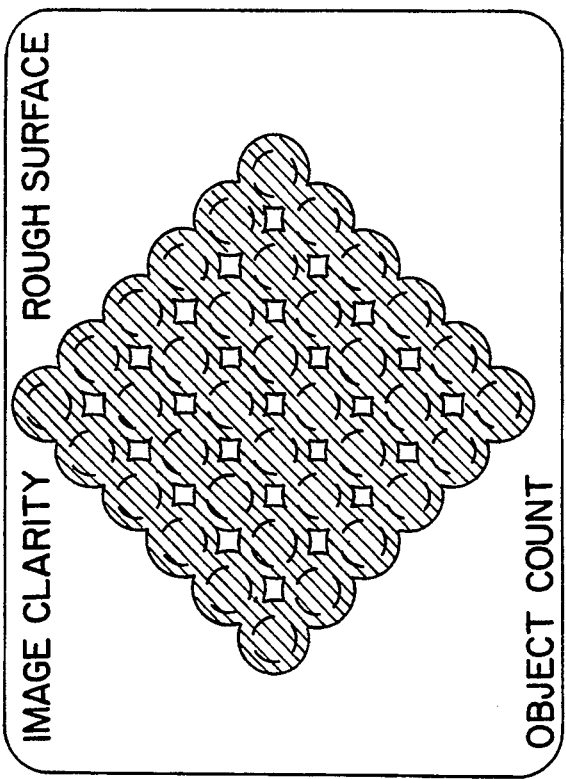
Figure 2E:
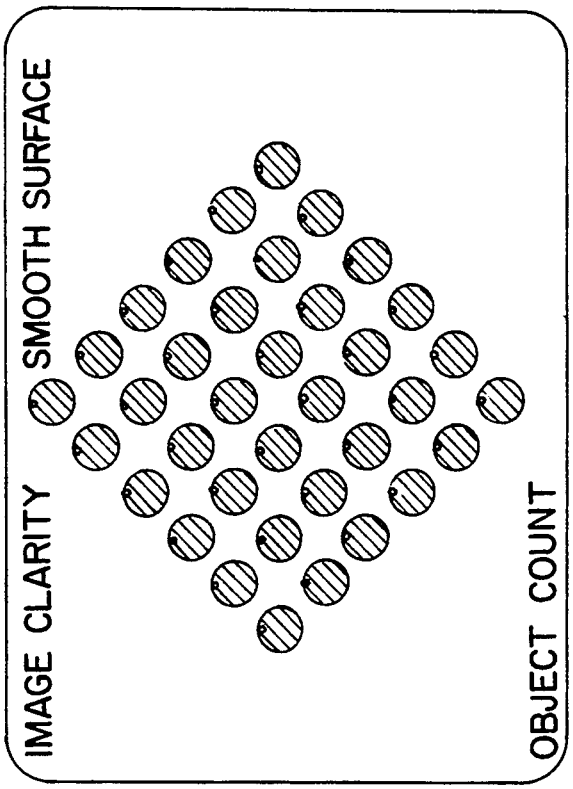

In FIG. 1 the image clarity of the surface (2) of the sheet (1) is determined. To this end an image forming element (4) is placed between the sheet (1) and a light source (3), which element (4) consists of a grid of, for example, 36 holes, each spaced approximately 1 mm apart. The image of this grid (4) is reflected by means of the light source (3) onto the surface (2) of the sheet (1), whereby a virtual image (8) of it is detected with a camera (5) and fed into a computer (6). In this computer (6) the necessary, processing takes place on the virtual image (8) of the projected image detected with the camera (5). The computer (6) shows the result of these computations on the output unit (7) as measurement signal indicating the image clarity of the sheet surface (2) of the sheet (1).

In FIGS. 2a-f show examples the measurement results are shown of a surface with a relatively good image clarity 2a (see left hand column) and of a surface with a relatively weak image clarity 2b (see right hand column). The images 2a and 2b relate to the virtual image (8) of the image of grid (4) projected onto surface (2) detected with the camera (5). The virtual image (8) detected by camera (5) is fed into the computer (6) where processing takes place which means that the detected virtual image (8) undergoes an image treatment, whereby the detected virtual image is split into a discrete number of image points from which per image point a discrete grey value is determined dependent on the light intensity of the virtual image (8) at the position of that image point, and that the number of distinct light spots of the virtual image (8) is determined by further treatment of the grey values pertaining to the image points.

Subsequently the virtual image (8) of the image projected onto the surface (2) is transformed into a binary image by determining a binary value for each image point by comparing the grey value determined at each image point with an adjustable discriminator value and where the grey value of that image point is equal or greater in relation to the discriminator value, by adjusting the binary value pertaining to that image point to a first of the binary values, and where the grey value of that image point is smaller in relation to the discriminator value, by adjusting the binary value pertaining to that image point to a second of the binary values.

The result of this treatment is the two images 2c and 2d.

Next, the two images 2c and 2f show the arrangement of one and the same discriminator value in the case of the surface with the relatively good image clarity 2e and of the surface with the relatively poor image clarity 2f. It can be clearly observed that with one and the same discriminator value for the relatively good surface 2e as many distinct spots are detected as is projected with grid (4) and the light source (3) onto the surface (2) of the sheet (1) and detected with the camera (5).

With 2f, the poor surface, on the other hand only one spot is detected, which is indeed provided with a number of holes, but this does not lead to a number of distinct spots greater than one. Consequently for this latter surface the discriminator value must still be re-adjusted and varied until the number of distinct spots in the binary image of the virtual image (8) of the image projected onto the surface (2) is equal to the number of distinct light spots which compose the image projected onto the surface (2). In the end this leads to a binary image that is comparable with FIG. 2c. The discriminator value pertaining to this is a measure for the signal that is presented as measure for the image clarity of the surface.

FIG. 3 shows results obtained by applying the method and apparatus of the invention on eight different sheets (a) through (h).

The arrangement of the discriminator value is plotted on the x-axis, and the y-axis shows the number of distinct light spots that are detected by the apparatus of the invention based on virtual image (8). The better quality sheets (d), (e), (f), (g) and (h) show that even at low values of the discriminator the number of light spots detected is greater than 1, and that with just a slight further increase in the discriminator value, the maximum number of light spots to be distinguished is reached (in this example 36 in due to the number of holes in image grid (4)). The sheets (a), (b) and (c) which possess a poorer image clarity show a clearly distinctive link between the trend of the discriminator value and the pertinent number of distinct light spots relating to the virtual image (8). It should also be noted here that, especially the distinction of the quality of sheet (c) relative to the quality of the sheets (d) through (h) which have a "better" surface takes place very simply and accurately, with the apparatus and method in accordance with the invention, while "visually" this is still found to be a problem.

We claim:

1. A method for determining the image clarity of a surface of a sheet or strip, comprising projecting an image on to a surface, detecting a virtual image of the image projected onto said surface and processing the detected virtual image into a signal which is presented as a measure of the image clarity of the surface, said image reflected onto the surface being composed of a two-dimensional array of distinct light spots, said processing of the detected virtual image comprising digitizing said detected virtual image with reference to at least one greyness discriminator value, and determining, for said greyness discriminator value, the number of distinct light spots in the digitized detected virtual image, and from said digitizing and said determining, obtaining a signal measuring image clarity of the whole area of the surface illuminated by said image projected onto the surface, said detected virtual image digitizing being performed for each of a plurality of said discriminator values and determining for each discriminator value the number of distinct spots in the virtual image, and wherein said signal that is presented as a measure of the image clarity of the surface is dependent on a relationship found between the discriminator values and the respective numbers of spots in the binary image.

2. The method in accordance with claim 1, comprising finding a greyness discriminator value at which the number of distinct spots determined in said virtual image is equal to the number of distinct light spots of said image projected onto the surface, said signal presented as a measure of the image clarity of the surface, being derived from said greyness discriminator value.

3. A method for determining the image clarity of a surface of a sheet or strip, comprising projecting an image on to a surface, detecting a virtual image of the image projected onto said surface and processing the detected virtual image into a signal which is presented as a measure of the image clarity of the surface, said image reflected onto the surface being composed of a two-dimensional array of distinct light spots, said processing of the detected virtual image comprising digitizing said detected virtual image with reference to at least one greyness discriminator value by separating said detected virtual image into a discrete number of image points and for each image point a discrete grey value is determined on a light intensity of the virtual image detected at the position of that image point, and determining, for said greyness discriminator value, the number of distinct light spots in the digitized detected virtual image by transforming the virtual image into a binary image by determining a binary value for each said image point by comparing the grey value determined at each image point with said discriminator value and assigning a binary value to each said image point in dependence on the result of this comparison, and from said digitizing and said determining, obtaining a signal measuring image clarity of the whole area of the surface illuminated by said image projected onto the surface, said digitizing of said detected virtual image being performed for each of a plurality of said discriminator values and determining for each discriminator value the number of distinct spots in the virtual image, and wherein said signal that is presented as a measure of the image clarity of the surface is dependent on a relationship found between the discriminator values and the respective numbers of spots in the binary image.

4. The method in accordance with claim 3, comprising finding a greyness discriminator value at which the number of distinct spots determined in said virtual image is equal to the number of distinct light spots of said image projected onto the surface, said signal presented as a measure of the image clarity of the surface, being derived from said greyness discriminator value.

5. Apparatus for determining the image clarity of a surface of a sheet or strip comprising means for reflecting an image onto the sheet, a receiver unit for detecting a virtual image of the image projected onto the surface and a processor unit provided with an output unit, which receiver unit is connected to the processor unit, said processor unit being a computer provided with a program for digitizing said detected virtual image with reference to at least one greyness discriminator value, and determining, for said greyness discriminator value, the number of distinct light spots in the digitized detected virtual image;

and from said digitizing and said determining, obtaining a signal measuring image clarity of the whole area of the surface illuminated by said image projected onto the surface, said digitizing of said detected virtual image being performed for each of a plurality of said discriminator values and determining for each discriminator value the number of distinct spots in the virtual image, and wherein said signal that is presented as a measure of the image clarity of the surface is dependent on a relationship found between the discriminator values and the respective numbers of spots in the binary image.

6. The apparatus in accordance with claim 5 wherein said computer is additionally programmed to find a greyness discriminator value at which the number of distinct spots determined in said virtual image is equal to the number of distinct light spots of said image projected onto the surface, said signal presented as a measure of the image clarity of the surface, being derived from said greyness discriminator value.

7. Apparatus for determining the image clarity of a surface of a sheet or strip comprising means for reflecting an image onto the sheet, a receiver unit for detecting a virtual image of the image projected onto the surface and a processor unit provided with an output unit, which receiver unit is connected to the processor unit, said processor unit being a computer provided with a program for digitizing said detected virtual image with reference to at least one greyness discriminator value, and determining, for said greyness discriminator value, the number of distinct light spots in the digitized detected virtual image;

and from said digitizing and said determining, obtaining a signal measuring image clarity of the whole area of the surface illuminated by said image projected onto the surface, said digitizing of said detected virtual image comprising separating said detected virtual image into a discrete number of image points and determining for each image point a discrete grey value dependent on a light intensity of the virtual image detected at the position of that image point, and wherein determining the number of distinct light spots in the digitized detected virtual image comprises transforming the virtual image into a binary image by determining a binary value for each said image point by comparing the grey value determined at each image point with said discriminator value and assigning a binary value to each said image point in dependence on the result of this comparison, said digitizing of said detected virtual image being performed for each of a plurality of said discriminator values and determining for each discriminator value the number of distinct spots in the virtual image, and wherein said signal that is presented as a measure of the image clarity of the surface is dependent on a relationship found between the discriminator values and the respective numbers of spots in the binary image.

8. The apparatus in accordance with claim 7, wherein said computer is additionally programmed to find a greyness discriminator value at which the number of distinct spots determined in said virtual image is equal to the number of distinct light spots of said image projected onto the surface, said signal presented as a measure of the image clarity of the surface, being derived from said greyness discriminator value.

* * * * *